(12) United States Patent
Shibata et al.

(10) Patent No.: US 7,531,631 B2
(45) Date of Patent: May 12, 2009

(54) METHOD FOR PREPARING HUMAN SERUM ALBUMIN THROUGH HEAT-TREATMENT IN THE PRESENCE OF DIVALENT CATION

(75) Inventors: Shinichi Shibata, Kikuchi (JP);
Kazuyuki Nakashima, Kikuchi (JP);
Tetsurou Tanabe, Kikuchi (JP);
Yoshinobu Miyatsu, Kikuchi (JP);
Hiroshi Mizokami, Kikuchi (JP)

(73) Assignee: Juridical Foundation the Chemoserotherapeutic Research Institute, Kumamoto (JP)

( * ) Notice: Subject to any disclaimer, the term of this patent is extended or adjusted under 35 U.S.C. 154(b) by 0 days.

(21) Appl. No.: 11/489,541

(22) Filed: Jul. 20, 2006

(65) Prior Publication Data
US 2006/0258850 A1 Nov. 16, 2006

Related U.S. Application Data

(63) Continuation of application No. PCT/JP2005/000647, filed on Jan. 20, 2005.

(30) Foreign Application Priority Data
Jan. 20, 2004 (JP) .............................. 2004-012054

(51) Int. Cl.
*C07K 14/00* (2006.01)
(52) U.S. Cl. ...................................... 530/364
(58) Field of Classification Search ....................... None
See application file for complete search history.

(56) References Cited

U.S. PATENT DOCUMENTS

2002/0182680 A1 12/2002 Nouchi et al.

FOREIGN PATENT DOCUMENTS

| EP | 0 073 646 A2 | 3/1983 |
|---|---|---|
| EP | 00886322 A2 | 9/1983 |
| EP | 0 420 007 A1 | 4/1991 |
| EP | 0 570 916 A2 | 11/1993 |
| EP | 0 650 736 A1 | 5/1995 |
| JP | 4-60639 B2 | 9/1992 |
| JP | 5-292993 B2 | 11/1993 |
| JP | 5-317079 A | 12/1993 |
| JP | 6-100592 A | 4/1994 |
| JP | 6-71434 B2 | 9/1994 |
| JP | 7-126182 A | 5/1995 |
| JP | 8-29111 B2 | 3/1996 |
| JP | 8-228790 A | 9/1996 |
| JP | 9-176195 A | 2/1999 |
| JP | 2885212 B2 | 2/1999 |
| JP | 11-509525 A | 8/1999 |
| JP | 2968052 B2 | 8/1999 |
| JP | 2002-128796 A | 5/2002 |
| WO | WO 96/37515 A1 | 11/1996 |

OTHER PUBLICATIONS

P.P. Minghetti, et al. "Molecular structure of the human albumin gene is revealed by nucleotide sequence within q11-22 of chromosome 4", J. Biol. Chem., 1986, 6747-6757, vol. 261 (15).
Alan V. Quirk, et al., "Production of Recombinant Human Serum Albumin from *Saccharomyces cerevisiae*", Biotechnology and Applied Biochemistry, 1989, 273-287, vol. 11 (3).
Ken Okabayashi et al., "Secretory Expression of the Human Serum Albumin Gene in the Yeast, *Saccharomyces cerevisiae*", J. Biochem., 1991, 103-110, vol. 110 (1).
Richard G. Buckholz and Martin A. Gleeson "Yeast Systems for the Commercial Production of Heterologous Proteins", Bio/Technology, 1991, 1067-1072, vol. 9 (11).
M. Latta et al., "Synthesis and purification of mature human serum albumin from *E-coli*", Bio/Technology, 1987, 1309-1314, vol. 5 (12).
C.W. Saunders et al., "Secretion of human serum albumin from *Bacillus subtilis*", J. Bacteriol., 1987, 2917-2925, vol. 169 (7).
M.W. Yu et al., "Stabilization of Human Alubumin by Caprylate and Acetyltryptophanate", Vox. Sang, 1984, 28-40, vol. 47.
J. Briggs et al., "Quantitation of DNA and Protein Impurities in Biopharmaceuticals", Anal. Chem., 1991, 850-859, vol. 63.
Hansen, et al., "A New High Quality Albumin for Therapeutic Use," *Develop. Biol. Standard* 48:105-112 (S. Karger, Basel 1981) XP-001079403.

*Primary Examiner*—Anand U Desai
(74) *Attorney, Agent, or Firm*—Sughrue Mion, PLLC

(57) ABSTRACT

The present invention herein discloses a method for purifying human serum albumin, which is characterized in that it comprises the steps of heat-treating a human serum albumin-containing solution including impurities originated from a host cell, in the presence of a divalent cation such as calcium ion, magnesium ion, nickel ion, cobalt ion, iron ion and zinc ion to thus selectively allow the impurities to undergo agglutination. The present invention also provides the highly purified human serum albumin prepared by the foregoing method.

35 Claims, No Drawings

US 7,531,631 B2

METHOD FOR PREPARING HUMAN SERUM ALBUMIN THROUGH HEAT-TREATMENT IN THE PRESENCE OF DIVALENT CATION

This application is a continuation of International Application No. PCT/JP2005/000647 filed on Jan. 20, 2005, claiming priority based on Japanese Application No. 2004-12054 filed on Jan. 20, 2004, the contents of all of which are incorporated herein by reference in their entirety.

TECHNICAL FIELD

The present invention relates to a method for the preparation of human serum albumin starting from a raw material obtained according to gene engineering technique. More specifically, the present invention pertains to a method for the preparation of human serum albumin which comprises the steps of heat-treating a human serum albumin-containing solution including impurities originated from a host cell in the presence of a divalent cation to thus selectively allow the impurities to undergo agglutination and removing aggregates thus generated through a low speed centrifugation or filtration treatment.

BACKGROUND ART

Human serum albumin is a principal protein component present in plasma, it consists of a single chain polypeptide containing 585 amino acids and it has a molecular weight of about 66,000 Dalton (Da) (see, for instance, Non-Patent Document 1 given below). Principally, it has been known that human serum albumin plays a role to maintain the normal osmotic pressure of a blood and that it can also serve as a carrier for transporting a variety of substances appearing in the blood such as calcium ion, fatty acids, bilirubin, tryptophan and drugs or it can be linked with the foregoing substances to thus transport the same. Purified human serum albumin is used for the treatment of, for instance, hypoalbuminemia caused due to the loss of albumin through, for instance, surgical operations, hemorrhagic shock, burn or nephrotic syndrome.

Conventionally, human serum albumin has been prepared from the human plasma by the Cohn's low-temperature ethanol fractionation technique or by a method comprising the steps of preparing a human serum albumin fraction (the human serum albumin is fractionated in the fraction V) according to the same fractionation technique and then purifying the fraction while making use of a variety of purification methods. However, this method suffers from problems in that it is difficult to secure a sufficient quantity of a raw material therefor and that the resulting human serum albumin may be contaminated with pathogens and accordingly, there has been desired for the development of a technique for the preparation of the human serum albumin which is not derived from human plasma. As a method for solving such a problem, there have recently been developed techniques for using yeast fungal cells (see Non-Patent Document Nos. 2, 3 and 4 given below); *Escherichia coli* cells (see Non-Patent Document Nos. 5 and 6 given below); *Bacillus subtilis* (see Non-Patent Document 7 given below); or animal cells to produce human serum albumin.

In this regard, the resulting human serum albumin can in general be purified by any one of purification techniques currently used in protein chemistry such as the salting out, ultrafiltration, isoelectric precipitation, electrophoresis, ion exchange chromatography, gel filtration chromatography or affinity chromatography technique. In fact, the human serum albumin thus obtained contains a plurality of proteins such as biological tissues, cells and blood in an admixed condition and therefore, the human serum albumin is purified according to a complicated combination of the foregoing purification techniques. These methods have been applied to the method for the preparation of human serum albumin starting from a raw material produced according to the gene-recombination technique (see, for instance, Patent Document Nos. 1, 2 and 3 specified below).

It has been well-known that a human serum albumin is stable against heat-treatment in the presence of acetyl tryptophan and caprylic acid (see, for instance, Non-Patent Document 8 given below). Such heat-stability characteristics of the human serum albumin have been incorporated into the process for the preparation of the same for the purpose of deactivation of any protease present in the supernatant of a culture medium (see, for instance, Patent Document 4 specified below) and likewise used in a method for the sterilization of a final pharmaceutical preparation (see, for instance, Patent Document 5 specified below). The heat-treating method used in the production process can be considered to be useful in that it can process a large quantity of a human serum albumin-containing solution.

In most of cases, a large quantity of human serum albumin is administered to a patient in the aforementioned treatments and therefore, possible side effects of impurities present therein become an important problem as compared with a vaccine or other drugs administered in a small amount. For this reason, the human serum albumin prepared through a gene engineering technique should have a purity extremely higher than those required for a vaccine or conventional preparations containing human serum albumin originated from plasma. Moreover, it is necessary to establish a preparation method which permits the treatment of a large quantity of a raw material at low cost while taking into consideration stable supply of a human serum albumin to the market.

Patent Document 1: Japanese Patent No. 2,885,212;
Patent Document 2: JP-T-Hei 11-509525;
Patent Document 3: JP-A-Hei 6-100592;
Patent Document 4: JP-B-Hei 6-71434;
Patent Document 5: JP-A-Hei 7-126182
Non-Patent Document 1: Minghetti, P. P. et al., "Molecular Structure of the human albumin gene is revealed by nucleotide sequence within q11-22 of chromosome 4.", J. Biol. Chem., 1986, 261:6747-6757;
Non-Patent Document 2: Alan V. Quirk, Michael J. Geisow et al., "Production of Recombinant Human Serum Albumin from *Saccharomyces cerevisiae*"; Biotechnology and Applied Biochemistry, 1989, 11:273-287;
Non-Patent Document 3: Ken Okabayashi, et al., "Secretory Expression of the Human Serum Albumin Gene in the Yeast, *Saccharomyces cerevisiae*"; J. Biochem., 1991, 110:103-110;
Non-Patent Document 4: Richard G. Buckholz and Martin A. G. Gleeson "Yeast Systems for the Commercial Production of Heterologous Proteins"; Bio/Technology, 1991, 9:1067-1072;
Non-Patent Document 5: Lawn, R. M., "Construction of DNA sequences and their use for microbial production of proteins, in particular, human serum albumin", "European Patent Appl.", 1983, 73:646;
Non-Patent Document 6: Latta, L. et al., Synthesis and purification of mature human serum albumin from *E. coli*; Biotechnique, 1897, 5:1309-1314;
Non-Patent Document 7: Saunders, C. W. et al., Secretion of human serum albumin from *Bacillus subtilis*, J. Bacteriol., 1987, 169:2917-2925;

Non-Patent Document 8: "Standard for Biological Preparations", pp. 285-289, Published on October 10, in Showa 60 (1985), Incorporated Body: Association of Bacterial Preparations.

DISCLOSURE OF THE INVENTION

Problems That the Invention is to Solve

It is an object of the present invention to provide a more effective method for the preparation of human serum albumin, which makes use of an improved heat-treating step incorporated into the same.

It is another object of the present invention to provide human serum albumin which can be prepared according to the foregoing preparation method and which has high safety as a medical product.

Means for Solving the Problems

The inventors of this invention have conducted various studies to achieve the foregoing objects and have found that if an ion selected from the group consisting of calcium ion, magnesium ion, nickel ion, cobalt ion, iron ion and zinc ion is added to a human serum albumin-containing solution including impurities originated from a host cell and the resulting mixture is then heat-treated, the impurities can thus selectively undergo agglutination and that the resulting aggregates can easily be removed by low speed centrifugation or filtration. Moreover, the inventors have likewise found that if such a heat-treatment is carried out while adding to the human serum albumin-containing solution, sodium caprylate currently known as a stabilizer against the heat-treatment, the impurities originated from the host cell are more efficiently undergo agglutination and have thus completed the present invention on the basis of the foregoing findings.

According to the present invention, there is provided a method for the preparation of human serum albumin as will be detailed below:

1. A method for purifying human serum albumin characterized in that it comprises the steps of heat-treating a human serum albumin-containing solution including impurities originated from a host cell in the presence of a divalent cation to thus selectively allow the impurities to undergo agglutination and then removing aggregates thus generated from the human serum albumin-containing solution.
2. A method for preparing human serum albumin starting from a raw material obtained through gene engineering operations characterized in that it comprises the steps of heat-treating a human serum albumin-containing solution including impurities originated from a host cell in the presence of a divalent cation to thus allow the impurities to undergo agglutination and then removing aggregates thus generated from the human serum albumin-containing solution.
3. A method for purifying human serum albumin characterized in that it comprises the steps of heat-treating a human serum albumin-containing solution including impurities originated from a host cell in the presence of a divalent cation and a stabilizer to thus allow the impurities to undergo agglutination and then removing aggregates thus generated from the human serum albumin-containing solution.
4. A method for preparing human serum albumin starting from a raw material obtained through gene engineering operations characterized in that it comprises the steps of heat-treating a human serum albumin-containing solution including impurities originated from a host cell in the presence of a divalent cation and a stabilizer to thus allow the impurities to undergo agglutination and then removing aggregates thus generated from the human serum albumin-containing solution.
5. The method as set forth in any one of the foregoing items 1 to 4 wherein the human serum albumin-containing solution has a human serum albumin concentration ranging from 0.01 to 30%.
6. The method as set forth in any one of the foregoing items 1 to 4 wherein the human serum albumin-containing solution has a human serum albumin concentration ranging from 0.1 to 10%.
7. The method as set forth in any one of the foregoing items 1 to 6 wherein the divalent cation is selected from the group consisting of calcium ion, magnesium ion, nickel ion, cobalt ion, iron ion and zinc ion.
8. The method as set forth in any one of the foregoing items 1 to 7 wherein the concentration of the divalent cation ranges from 1 to 1000 mM.
9. The method as set forth in any one of the foregoing items 1 to 7 wherein the concentration of the divalent cation ranges from 100 to 500 mM.
10. The method as set forth in any one of the foregoing items 3 to 9 wherein the stabilizer is acetyl tryptophan or a salt thereof and/or a fatty acid (having 6 to 20 carbon atoms) or a salt thereof.
11. The method as set forth in the foregoing item 10 wherein the fatty acid salt is sodium caprylate.
12. The method as set forth in the foregoing item 11 wherein the concentration of the sodium caprylate ranges from 5 to 20 mM.
13. The method as set forth in any one of the foregoing items 1 to 12 wherein the heat-treatment is carried out at a temperature ranging from 50 to 95° C.
14. The method as set forth in any one of the foregoing items 1 to 12 wherein the heat-treatment is carried out at a temperature ranging from 60 to 75° C.
15. The method as set forth in any one of the foregoing items 1 to 14 wherein the heat-treatment is carried out for a time ranging from one minute to 30 hours.
16. The method as set forth in any one of the foregoing items 1 to 14 wherein the heat-treatment is carried out for a time ranging from 1 to 5 hours.
17. The method as set forth in any one of the foregoing items 1 to 16 wherein the heat-treatment is carried out at a pH value ranging from 4.5 to 10.
18. The method as set forth in any one of the foregoing items 1 to 16 wherein the heat-treatment is carried out at a pH value ranging from 9 to 10.
19. The method as set forth in any one of the foregoing items 1 to 18 wherein the step for the removal of the aggregates includes the use of a low speed centrifugation technique, an ultrafiltration technique whose fractional molecular weight ranges from 100,000 to 300,000, or the combination of these techniques.
20. A method for preparing human serum albumin starting from a raw material obtained through gene engineering operations characterized in that it comprises the following steps:
(1) Heat-treating a human serum albumin-containing solution including impurities originated from a host cell and having a human serum albumin concentration ranging from 5 to 10%, in the presence of calcium ion in an amount ranging from 100 to 500 mM, while optionally adding sodium caprylate in an amount ranging from 5 to 20 mM, at a pH value ranging from 9 to 10 and a temperature ranging from 60 to 75° C. for a time ranging from 1 to 5 hours to thus allow the impurities to undergo agglutination; and (2) removing aggregates thus generated from the human serum albumin-containing solution using a low speed centrifugation technique, an ultrafiltration technique whose fractional molecular weight ranges from 100,000 to 300,000, or the combination of these techniques.

According to the present invention, there is also provided highly purified human serum albumin prepared by the foregoing methods.

Effects of the Invention

According to the present invention, there is thus provided a method for the heat-treatment of a human serum albumin-containing solution contaminated with impurities, which are originated from plasma or a host cell in the presence of a divalent cation. This method permits the selective agglutination of the impurities and the resulting aggregates can easily be removed through a low speed centrifugation technique or a filtration technique. The method of the present invention is quite simple and permits the treatment of a large quantity of such a human serum albumin-containing solution at a time. In addition, the human serum albumin obtained by the method of the present invention is a highly purified product almost completely free of any impurity and accordingly, it can be used in the preparation of an antibody against the human serum albumin and as a constituent element for a variety of agents for detection which uses an antigen-antibody reaction.

Best Mode for Carrying Out the Invention

The method of the present invention is characterized in that a human serum albumin-containing solution including impurities originated from a host cell is heat-treated in the presence of a divalent cation and that the resulting aggregates of the impurities are then removed. The implementation of this method would permit the efficient preparation of highly purified human serum albumin substantially free of such impurities originated from the host cell.

The human serum albumin-containing solution to be subjected to the foregoing heat-treatment is not restricted to any particular one in as much as it is a recombinant human serum albumin (hereafter also referred to as "rHA")-containing solution produced by the gene engineering technique. The present invention relates to a method for heat-treating an rHA-containing solution produced by the gene engineering technique, but it may likewise be applied to the treatment of the human serum albumin derived from plasma (hereafter also referred to as "HSA").

Usable herein as the rHA-containing solutions may be a culture supernatant obtained by cultivating a human serum albumin-producing cell established by the gene engineering technique or a solution containing crushed the human serum albumin-producing cells. Examples of host cells usable in the present invention for the production of the rHA-containing solutions include yeast fungi, *Escherichia coli, Bacillus subtilis* and animal cells, but preferably used herein are, for instance, yeast fungi such as those belonging to the genus *Saccharomyces* or the genus *Pichia*. More preferably used herein include, for instance, *Saccharomyces cerevisiae* AH22 strains ([cir+, a, Leu2, His4, can1], hereafter also referred to as "AH22 strains") or mutant strains thereof.

The preparation of human serum albumin-producing yeast cells, the cultivation thereof and the isolation and collection of rHA may be carried out according to any known methods. Usable herein as such known techniques include, for instance, a method for cloning a human serum albumin-encoding gene (Japanese Patent No. 1,896,877); the establishment of an expression vector containing a gene coding for human serum albumin, the transformation of yeast cells with the expression vector, the cultivation of the yeast cells thus transformed and a method for recovering the resulting human serum albumin (Japanese Patent No. 2,968,052); a method for the preparation of secretory rHA-producing yeast cells (Japanese Patent No. 2,136,547); a method for the preparation of mutant rHA-encoding gene (JP-A-Hei 8-228790); and a method for purifying rHA from the culture media of rHA-producing yeast cells (Patent Document Nos. 2 and 3).

In practice, when preparing yeast mutant cells, cloning the rHA-encoding gene, and establishing an expression vector, it is sufficient to use a commercially available kit. For instance, the following are put on the market, reagents such as TRIzol reagents (available from Invitrogen Corporation), ISOGEN (available from Nippon Gene Company), StrataPrep Total RNA Purification Kit (available from Toyobo Co., Ltd.) for the RNA extraction; kits such as mRNA Purification Kit (available from Amersham Bioscience Company), Poly(A) Quick mRNA Isolation Kit (available from Toyobo Co., Ltd.) and mRNA Separator Kit (available from Clontech Company) for the purification of mRNA; and SuperScript plasmid system for cDNA synthesis and plasmid cloning (available from Invitrogen Corporation), cDNA Synthesis Kit (available from Takara Shuzo Co., Ltd.), SMART PCR cDNA Synthesis & Library Construction Kits (available from Clontech Company), Directionary cDNA Library Construction systems (available from Novagene Company) or the like for the conversion into cDNA. It is also possible to prepare an intended gene by a chemical synthesis method.

When the yeast cells are transformed by using the rHA-expression vector, there may be used, for instance, techniques commonly used frequently such as the protoplast-polyethylene glycol fusion technique and the electroporation technique.

In the cultivation of the rHA-producing yeast cells, there can be used, for instance, YNB liquid culture medium as a selective medium and YPD liquid culture medium as a chemically defined medium. The cultivation method and cultivation conditions may arbitrarily be selected while taking into consideration the scale of the intended cultivation system, but the cultivation may fundamentally be carried out according to the methods currently used in the cultivation of microorganisms such as the batchwise cultivation techniques and the fed-batch type cultivation techniques. More specifically, the rHA-producing recombinant yeast cells are, in consecutive order, subjected to subculture in a selective chemically defined medium to thus give a pre-cultivated medium. The resulting pre-cultivated medium is then inoculated on a chemically defined medium in serial order, followed by the fed-batch cultivation at 30° C. for 70 to 90 hours to thus proliferate the rHA-producing cells. Thereafter, the culture product containing rHA thus produced is then subjected to purification processes.

When purifying rHA from the culture product of the rHA-producing yeast cells, the culture supernatant or the solution containing crushed yeast cells, the methods disclosed in, for instance, Patent Document Nos. 2 and 3 can be applied. Examples of such methods include purification techniques such as a treatment with an ultrafiltration membrane, a cation-exchange chromatography technique, an anion-exchange chromatography technique, a treatment with an acid, a heat-treatment, a hydrophobic chromatography technique, an adsorption chromatography technique, a gel filtration technique, an affinity chromatography technique, and a salting out technique. The conditions for the foregoing purification steps in practicing the rHA-production process may arbitrarily be selected depending on various factors such as the amount and concentration of the rHA-containing solution to be treated, the content of impurities present therein and the order or position of each specific step in the production process.

The heat-treatment used in the present invention may be carried out in any stage of the rHA-production process and over any desired number of times. In the heat-treatment, preferably used are rHA-containing solutions or HSA-containing solutions each having an rHA or HSA concentration ranging from 0.01 to 30% (w/v) and more preferably 0.1 to 10%. Examples of a divalent cation used in the heat-treatment include calcium ion, magnesium ion, nickel ion, cobalt ion, iron ion and zinc ion. Preferably used herein are calcium ion. In addition, examples of compounds constituting such a divalent cation include calcium chloride, magnesium chloride and magnesium sulfate. The divalent cation is used in a concentration ranging from 1 to 1000 mM and more preferably 100 to 500 mM. The pH value of the solution upon the heat-treatment is preferably not less than 4.5, which is the lower limit for the dissolution of the caprylic acid salt, and not more than 11 at which the solution undergoes gelation and the pH value thereof more preferably ranges from 9 to 10. The heat-treatment is preferably carried out at a temperature ranging from 50 to 95° C. and more preferably 60 to 75° C. The heat-treatment is preferably carried out for a time ranging from one minute to 30 hours, but the treating time may be changed depending on the order of the heat-treating step in the overall rHA-production process. For instance, when the heat-treating step is carried out at an initial stage of the production process, the reduction of the production time has priority to the rate of removing impurities, while the heat-treating step is carried out in the latter half of the production process, it is preferential or important that impurities are eliminated as much as possible. Thus, the heat-treating time is set at a level while taking into consideration impurity-removing rate, but heat-treating time more preferably ranges from 1 to 5 hours. The heat-treatment of the present invention is more preferably carried out under the following combination of conditions: the rHA concentration of an rHA-containing solution used ranging from about 5 to 10%; the concentration of calcium chloride ranging from 100 to 500 mM; the pH value of the solution ranging from 9 to 10; the heat-treating temperature ranging from 60 to 75° C.; and the heat-treating time ranging from 1 to 5 hours.

More improved effects can be anticipated if the heat-treatment of the present invention is carried out in the presence of acetyl tryptophan or a salt thereof and/or a fatty acid (having 6 to 20 carbon atoms) or a salt thereof, which have been known as stabilizers for the albumin. These stabilizers are desirably used in a concentration falling within the range specified in Non-Patent Document 8 and Patent Document Nos. 1, 4 and 5. For instance, it is suitable for the heat-treatment of the present invention to use sodium caprylate in a concentration ranging from 5 to 20 mM.

The aggregates of impurities originated from the host cell formed through the heat-treatment of the present invention can be removed by, for instance, the treatment with an ultrafiltration membrane immediately after the heat-treatment. An ultrafiltration membrane whose fractional molecular weight preferably ranges from 100,000 to 300,000 is used. In addition, the aggregates can efficiently be removed by the use of a combination of the treatment with an ultrafiltration membrane and another method. Examples of other methods to remove the aggregates include centrifugation technique, in particular, a low speed centrifugation technique (for instance, the rotational speed thereof ranging from 2,000 to 3,000 rpm), and filtration (for instance, the filtration through a sterilized filter having a φ of 0.22 μm). The conditions for practicing these methods may appropriately be set at levels while taking into consideration, for instance, the scale of the production process, the kinds of coexisting impurities and the size of the resulting aggregates, but these methods are carried out under the conditions similar to those currently used for the purification of proteins. For instance, it is common to use a method in which the majority of the aggregates generated through the heat-treatment are removed by centrifugation and then the resulting supernatant is further treated by ultrafiltration technique.

The content of proteins as impurities originated from the host cell can be determined by an enzyme immunoassay technique (EIA method) and that of the polysaccharides present therein can be determined by a phenol-sulfuric acid method, respectively. The general protocols for these methods are disclosed in, for instance, "Antibodies a laboratory manual" (Ed Harlow.David Lane, Cold Spring Harbor Laboratory 1988) and Experimental Methods in Biology and Chemistry 23: Methods of Studying Sugar Chains of Glycoproteins (edited by TAKAHASHI Reiko, issued by Gakkai Publishing Center), respectively. In addition, the extent of the coloration of the rHA-containing solution can be examined by the determination of the absorbance thereof (OD350/A280, 450/A280, 500/A280). The content of impurity proteins originated from the host cell can be determined by, for instance, the culture media of yeast cells free of any albumin-producing ability are partially purified through the cation-exchange chromatography and rabbits are then immunized with the partially purified culture media to thus give an antiserum, followed by the detection of the impurities originated from the host cell and present in the albumin-containing solution which has been subjected to the heat-treatment and the removal of aggregates, while using the resulting antiserum. The EIA method used in the Examples of the present invention has a protein-quantity limit of 0.008 μg per unit amount (1 g) of rHA.

EXAMPLE 1

Heat-Treatment of Partially Purified Human Serum Albumin-Containing Solution in the Presence of Calcium Ion (1) Cultivation of rHA-Producing Recombinant Yeast Cells rHA-producing recombinant yeast cells (*Saccharomyces cerevisiae*) were in order sub-cultivated in a selective chemically defined medium to thus give a precultivated medium. The precultivated medium was then inoculated in a chemically defined medium in consecutive order, subjected to the fed-batch culture at 30° C. for 70 to 90 hours to thus make the rHA-producing cells proliferate.

(2) Partial Purification of rHA-Containing Solution

The foregoing cultured medium was diluted two times with purified water, followed by the addition of sodium caprylate to a final concentration of 5 mM and the adjustment of the pH value thereof to 4.5 with acetic acid. The resulting solution was adsorbed on an expanded bed cation-exchanger which had been equilibrated, in advance, with an acetate buffer (pH 4.5), followed by the elution with a phosphate buffer solution (pH 9.0) containing 300 mM of sodium chloride. The pH value of the resulting eluate was controlled to 9.0 with a 0.5N sodium hydroxide solution and then the eluate was allowed to stand over 5 hours. The eluate was then exchanged to a phosphate buffer (pH 5.5) containing 5 mM of caprylic acid, followed by the concentration thereof to a human serum albumin concentration of 10% (w/v), the heat-treatment of the resulting concentrate at 60° C. for one hour and the centrifugation to give a supernatant, which was used as a partially purified rHA-containing solution. The content of impurities of the partially purified rHA-containing solution was 1195.8 (µg/g rHA).

(3) Heat-Treatment of Partially Purified rHA-Containing Solution (in the presence of Ca ion)

To 4 mL of the partially purified rHA-containing solution (having an impurities content of 1195.8 µg/g rHA) prepared in the foregoing step (2), there was added 20 to 400 µL of a 1M calcium chloride solution, followed by the control of the pH value thereof to 5.5 with a 0.5N sodium hydroxide solution and heating of the resulting mixture at 60° C. for one hour. The heat-treated mixture was centrifuged at 3000 rpm for 30 minutes, the resulting supernatant was dialyzed against purified water and the resulting dialyzate was used in the enzyme immunoassay. The results thus obtained are summarized in the following Table 1 together with the rate of removed impurities. The rate of removed impurities was determined according to the following equation:

Rate of removed impurities (%)=100×$(A-B)/A$

A=The content of impurities present in an rHA-containing solution to be examined before the heat-treatment; and B=The content of impurities present in the rHA-containing solution after the heat-treatment.

TABLE 1

| Ca Ion Conc. (mM) | Content of impurities detected after heat-treatment (µg/g rHA) | Rate of removed impurities (%) |
|---|---|---|
| 0 | 788 | 34.1 |
| 5 | 683 | 42.9 |
| 50 | 475 | 60.3 |
| 100 | 205 | 82.9 |

(4) Heat-Treatment of Partially Purified rHA-Containing Solution (in the Presence of Ca Ion and Caprylic Acid)

To 4 mL of the partially purified rHA-containing solution (having an impurities content of 1195.8 µg/g rHA) prepared in the foregoing step (2), there were added 20 to 400 µL of a 1M calcium chloride solution and 30 µL of a 2M caprylic acid solution, followed by the control of the pH value thereof to 5.5 with a 1% acetic acid solution and heating of the resulting mixture at 60° C. for one hour. The heat-treated mixture was centrifuged at 3000 rpm for 30 minutes, the resulting supernatant was dialyzed against purified water and the resulting dialyzate was used in the enzyme immunoassay. The results thus obtained are summarized in the following Table 2 together with the rate of removed impurities.

TABLE 2

| Ca Ion Conc. (mM) | Content of impurities detected after heat-treatment (µg/g rHA) | Rate of removed impurities (%) |
|---|---|---|
| 0 | 322 | 73.1 |
| 5 | 230 | 80.8 |
| 50 | 111 | 90.7 |
| 100 | 91 | 92.4 |

EXAMPLE 2

Heat-Treatment, With Time, of Partially Purified Human Serum Albumin-Containing Solution in the Presence of Calcium Ion (1) Cultivation of rHA-Producing Recombinant Yeast Cells rHA-producing recombinant yeast cells (*Saccharomyces cerevisiae*) were in order sub-cultivated in a selective chemically defined medium to thus give a precultivated medium. The precultivated medium was then inoculated in a chemically defined medium in consecutive order, subjected to the fed-batch culture at 30° C. for 70 to 90 hours to thus make the rHA-producing cells proliferate.

(2) Partial Purification of rHA-Containing Solution

The foregoing cultured medium was diluted two times with purified water, followed by the addition of sodium caprylate to a final concentration of 5 mM and the adjustment of the pH value thereof to 4.5 with acetic acid. The resulting solution was adsorbed on an expanded bed cation-exchanger which had been equilibrated, in advance, with an acetate buffer (pH 4.5), followed by the elution with a phosphate buffer solution (pH 9.0) containing 300 mM of sodium chloride. The pH value of the resulting eluate was controlled to 9.0 with a 0.5N sodium hydroxide solution and then the eluate was allowed to stand over 5 hours. The eluate was then concentrated to an rHA concentration of about 10% (w/v) using an ultrafiltration membrane whose molecular cutoff was set at 10 KDa, the resulting concentrate was then diluted 5 times with purified water and the diluted rHA-containing solution was again concentrated to an rHA concentration of about 10% (w/v), which was used as a partially purified rHA-containing solution. The content of impurities of the partially purified rHA-containing solution was 72,145 (µg/g rHA).

(3) Heat-Treatment of Partially Purified rHA-Containing Solution (in the Presence of Ca Ion and Na Caprylate)

5 mL of the partially purified rHA-containing solution (having an impurities content of 72,145 µg/g rHA) prepared in the foregoing step (2) in Example 2 were heat-treated at 60° C., a pH value of 9.5 for 1 to 24 hours in the presence of calcium chloride and sodium caprylate in final concentrations of 100 mM and 20 mM, respectively. The heat-treated mixture was centrifuged at 3000 rpm for 30 minutes. The resulting supernatant was dialyzed against purified water and the resulting dialyzate was used in the enzyme immunoassay. The results thus obtained are summarized in the following Table 3 together with the rate of removed impurities.

TABLE 3

| Heat-Treatment (Ca + Na Caprylate) (hours) | Content of impurities detected after heat-treatment (µg/g rHA) | Rate of removed impurities (%) |
|---|---|---|
| 1 | 56.6 | 99.92 |
| 2 | 43.3 | 99.94 |
| 3 | 35.0 | 99.95 |
| 5 | 29.2 | 99.96 |
| 10 | 27.5 | 99.96 |
| 24 | 19.0 | 99.97 |

(4) Heat-Treatment of Partially Purified rHA-Containing Solution (in the Presence of Ca Ion and Na Caprylate)

5 mL of the partially purified rHA-containing solution (having an impurities content of 60,146 µg/g rHA) prepared in the foregoing step (2) in Example 2 were heat-treated at a temperature ranging from 50 to 80° C., a pH value of 9.5 for 1 to 60 minutes in the presence of 20 mM sodium caprylate and in the presence or absence of calcium chloride in a final concentration of 100 mM. The heat-treated mixture was centrifuged at 3000 rpm for 30 minutes. The resulting supernatant was dialyzed against purified water and the resulting dialyzate was used in the enzyme immunoassay. The results thus obtained are summarized in the following Table 4 together with the rate of removed impurities.

TABLE 4

| Heating Temp. | Heating Time (min) | Content of impurities detected after heat-treatment (μg/g rHA) | | Rate of removed impurities (%) | |
|---|---|---|---|---|---|
| | | Ca⁻ | Ca+ | Ca⁻ | Ca+ |
| 50° C. | 1 | 44036 | 41464 | 26.78 | 31.06 |
| 50° C. | 30 | 36493 | 17596 | 39.33 | 70.74 |
| 50° C. | 60 | 21101 | 5997 | 64.92 | 90.03 |
| 60° C. | 1 | 2253 | 1168 | 96.25 | 98.06 |
| 60° C. | 30 | 1138 | 182 | 98.11 | 99.70 |
| 60° C. | 60 | 972 | 323 | 98.38 | 99.46 |
| 70° C. | 1 | 940 | 194 | 98.44 | 99.68 |
| 70° C. | 30 | 201 | 21 | 99.67 | 99.97 |
| 80° C. | 1 | 1007 | 229 | 98.33 | 99.62 |

EXAMPLE 3

Heat-Treatment of Human Serum Albumin-Containing Solution in the Presence of Divalent Ion (1) Partial Purification of rHA-Containing Solution The cultured medium prepared in the step (1) in Example 2 was diluted two times with purified water, followed by the addition of sodium caprylate to a final concentration of 5 mM and the adjustment of the pH value thereof to 4.5 with acetic acid. The resulting solution was adsorbed on an expanded bed cation-exchanger which had been equilibrated, in advance, with an acetate buffer (pH 4.5), followed by the elution with a phosphate buffer solution (pH 9.0) containing 300 mM of sodium chloride. The pH value of the resulting eluate was controlled to 9.0 with a 0.5N sodium hydroxide solution and then the eluate was allowed to stand over 5 hours. The eluate was then concentrated to an rHA concentration of about 10% (w/v). The resulting concentrate was exchanged to a phosphate buffer solution (pH 5.5) containing 20 mM of caprylic acid and the resulting product was used as a partially purified rHA-containing solution. The Content of impurities of partially purified rHA-containing solution was 67,182 (μg/g rHA).

(2) Heat-Treatment of Partially Purified rHA-Containing Solution 4 mL of the foregoing partially purified rHA-containing solution (having an impurities content of 67,182 μg/g rHA) were heat-treated at 60° C., a pH value of 5.5 for one hour in the presence of 50 mM of a divalent cation. The heat-treated mixture was centrifuged at 3000 rpm for 30 minutes and the resulting supernatant was filtered. Then the resulting filtrate was dialyzed against purified water and the resulting dialyzate was used in the enzyme immunoassay. The results thus obtained are summarized in the following Table 5 together with the rate of removed impurities.

TABLE 5

| Kind of Ion | Content of impurities detected after heat-treatment (μg/g rHA) | Rate of removed impurities (%) |
|---|---|---|
| Free of any added ion | 1156 | 98.28 |
| Calcium ion | 420 | 99.37 |
| Magnesium ion | 828 | 98.77 |
| Cobalt ion | 345 | 99.49 |
| Nickel ion | 572 | 99.15 |
| Iron ion | 555 | 99.17 |
| Zinc ion | 920 | 98.63 |

EXAMPLE 4

Heat-Treatment of Highly Purified Human Serum Albumin-Containing Solution in the Presence of Calcium Ion (1) Advanced Purification of rHA-Containing Solution The partially purified rHA-containing solution obtained in Example 1 was applied to a cation exchanger, which had been equilibrated, in advance, with a phosphate buffered solution (pH 5.5) containing 5 mM of caprylic acid. To the fraction passed through the cation exchanger without being adsorbed thereon, there were added 1M of sodium chloride and then sodium chloride and a 0.5N sodium hydroxide solution such that the pH value thereof reached 7.0 and then the resulting mixture was applied to a hydrophobic chromatography carrier, which had been equilibrated, in advance, with a phosphate buffered solution (pH 7.0) containing 1M of sodium chloride. The fraction passed through the hydrophobic chromatography carrier without being adsorbed thereon was exchanged to a glycine buffer solution (pH 8.45) containing 100 mM of sodium chloride and 50 mM of calcium chloride and then loaded on a affinity chromatography carrier, which had been equilibrated, in advance, with a buffer solution similar to that used above. The fraction passed through the affinity chromatographic carrier without being adsorbed thereon was concentrated to an rHA concentration of about 10% and then diluted 4 times with purified water and the resulting diluted solution was hereafter used as a highly purified rHA-containing solution.

(2) Heat-Treatment 1 of Highly Purified rHA-Containing Solution (in the Presence of Ca Ion and Na Caprylate)

The foregoing highly purified rHA-containing solution (impurity content: 13.35 μg/g rHA) was heat-treated at 60° C. for one hour in the presence of 100 to 1000 mM of calcium ion and 20 mM of sodium caprylate. The heat-treated solution was then centrifuged at 3000 rpm for 30 minutes and the resulting supernatant was filtered. The resulting filtrate was dialyzed against purified water and then used in the enzyme immunoassay. The results thus obtained are summarized in the following Table 6 together with the rate of removed impurities.

TABLE 6

| Ca ion Conc. (mM) | Content of impurities detected after heat-treatment (μg/g rHA) | Rate of removed impurities (%) |
|---|---|---|
| 100 | 0.069 | 99.48 |
| 250 | 0.032 | 99.76 |
| 500 | Not more than the quantity limit | Not less than 99.83 |

TABLE 6-continued

| Ca ion Conc. (mM) | Content of impurities detected after heat-treatment (µg/g rHA) | Rate of removed impurities (%) |
| --- | --- | --- |
| 750 | Not more than the quantity limit | Not less than 99.73 |
| 1000 | Not more than the quantity limit | Not less than 99.03 |

(3) Heat-Treatment 2 of Highly Purified rHA-Containing Solution (in the Presence of Ca Ion and Na Caprylate)

The foregoing highly purified rHA-containing solution (impurity content: 21.265 µg/g rHA) was heat-treated at 60° C. for one hour or 16 hours in the presence of 100 mM of calcium ion and 20 mM of sodium caprylate. The heat-treated solution was then centrifuged at 3000 rpm for 30 minutes and the resulting supernatant was filtered. The resulting filtrate was dialyzed against purified water and then used in the enzyme immunoassay. The results thus obtained are summarized in the following Table 7 together with the rate of removed impurities.

TABLE 7

| Heat-Treatment Time (Hr.) | Content of impurities detected after heat-treatment (µg/g rHA) | Rate of removed impurities (%) |
| --- | --- | --- |
| 1 | 0.085 | 99.60 |
| 16 | Not more than the quantity limit | Not less than 99.88 |

INDUSTRIAL APPLICABILITY

Calcium chloride used in the present invention is a less expensive compound and the use thereof would permit the significant reduction of the production cost of human serum albumin. According to the method of the present invention, there can thus be provided highly purified human serum albumin substantially free of any impurity originated from a host cell, which may become a cause of side-effects such as shock and/or allergy when administering the same to a person and the resulting highly purified human serum albumin can be used as an agent for the treatment of, for instance, hypoalbuminemia caused due to the loss of albumin through, for instance, surgical operations, hemorrhagic shock, burn or nephrotic syndrome and it may likewise be used as a stabilizer for a variety of active proteins and vaccines.

What is claimed is:

1. A method for purifying human serum albumin characterized in that it comprises the steps of heat-treating at a pH value ranging from 5.5 to 10.0 a human serum albumin-containing solution including impurities originated from a host cell in the presence of a divalent cation and a stabilizer to thus allow the impurities to undergo agglutination and then removing aggregates thus generated from the human serum albumin-containing solution.

2. A method for producing human serum albumin starting from a raw material obtained through gene engineering operations characterized in that it comprises the steps of heat-treating at a pH value ranging from 5.5 to 10.0 a human serum albumin-containing solution including impurities originated from a host cell in the presence of a divalent cation and a stabilizer to thus allow the impurities to undergo agglutination and then removing aggregates thus generated from the human serum albumin solution.

3. The method as set forth in claim 1 wherein the human serum albumin-containing solution has, before the heat-treating, a human serum albumin concentration ranging from 0.01 to 30%.

4. The method as set forth in claim 1 wherein the human serum albumin-containing solution has, before heat-treating, a human serum albumin concentration ranging from 0.1 to 10%.

5. The method as set forth in claim 1 wherein the divalent cation is selected from the group consisting of calcium ion, magnesium ion, nickel ion, cobalt ion, iron ion and zinc ion.

6. The method as set forth in claim 1 wherein the concentration of the divalent cation ranges from 1 to 1000 mM.

7. The method as set forth in claim 1 wherein the concentration of the divalent cation ranges from 100 to 500 mM.

8. The method as set forth in claim 1 wherein the stabilizer is acetyl tryptophan or a salt thereof and/or a fatty acid having 6 to 20 carbon atoms or a salt thereof.

9. The method as set forth in claim 8 wherein the fatty acid salt is sodium caprylate.

10. The method as set forth in claim 9 wherein the concentration of the sodium caprylate ranges from 5 to 20 mM.

11. The method as set forth in claim 1 wherein the heat-treatment is carried out at a temperature ranging from 50 to 95° C.

12. The method as set forth in claim 1 wherein the heat-treatment is carried out at a temperature ranging from 60 to 75° C.

13. The method as set forth in claim 1 wherein the heat-treatment is carried out for a time ranging from one minute to 30 hours.

14. The method as set forth in claim 1 wherein the heat-treatment is carried out for a time ranging from 1 to 5 hours.

15. The method as set forth in claim 1 wherein the heat-treatment is carried out at a pH value ranging from 9 to 10.

16. The method as set forth in claim 1 wherein the step for the removal of the aggregates includes the use of a low speed centrifugation technique, an ultrafiltration technique whose fractional molecular weight ranges from 100,000 to 300,000, or the combination of these techniques.

17. A method for preparing human serum albumin starting from a raw material obtained through gene engineering operations characterized in that it comprises the following steps:
    (1) heat-treating a human serum albumin-containing solution including impurities originated from a host cell and having a human serum albumin concentration ranging, before heat-treating, from 5 to 10%, in the presence of calcium ion in an amount ranging from 100 to 500 mM, while optionally adding sodium caprylate in an amount ranging from 5 to 20 mM, at a pH value ranging from 9 to 10 and a temperature ranging from 60 to 75° C. for a time ranging from 1 to 5 hours to thus allow the impurities to undergo agglutination; and
    (2) removing aggregates thus generated from the human serum albumin-containing solution using a low speed centrifugation technique, an ultrafiltration technique whose fractional molecular weight ranges from 100,000 to 300,000, or the combination of these techniques.

18. The method as set forth in claim 2 wherein the human serum albumin-containing solution has, before the heat-treating, a human serum albumin concentration ranging from 0.01 to 30%.

19. The method as set forth in claim 2 wherein the human serum albumin-containing solution has, before heat-treating, a human serum albumin concentration ranging from 0.1 to 10%.

20. The method as set forth in claim 2 wherein the divalent cation is selected from the group consisting of calcium ion, magnesium ion, nickel ion, cobalt ion, iron ion and zinc ion.

21. The method as set forth in claim 2 wherein the concentration of the divalent cation ranges from 1 to 1000 mM.

22. The method as set forth in claim 2 wherein the concentration of the divalent cation ranges from 100 to 500 mM.

23. The method as set forth in claim 2 wherein the stabilizer is acetyl tryptophan or a salt thereof and/or a fatty acid having 6 to 20 carbon atoms or a salt thereof.

24. The method as set forth in claim 23 wherein the fatty acid salt is sodium caprylate.

25. The method as set forth in claim 24 wherein the concentration of the sodium caprylate ranges from 5 to 20 mM.

26. The method as set forth in claim 2 wherein the heat-treatment is carried out at a temperature ranging from 50 to 95° C.

27. The method as set forth in claim 2 wherein the heat-treatment is carried out at a temperature ranging from 60 to 75° C.

28. The method as set forth in claim 2 wherein the heat-treatment is carried out for a time ranging from one minute to 30 hours.

29. The method as set forth in claim 2 wherein the heat-treatment is carried out for a time ranging from 1 to 5 hours.

30. The method as set forth in claim 2 wherein the heat-treatment is carried out at a pH value ranging from 9 to 10.

31. The method as set forth in claim 2 wherein the step for the removal of the aggregates includes the use of a low speed centrifugation technique, an ultrafiltration technique whose fractional molecular weight ranges from 100,000 to 300,000, or the combination of these techniques.

32. A method for purifying human serum albumin characterized in that it consists of the steps of heat-treating at a pH value ranging from 5.5 to 10.0 a human serum albumin-containing solution including impurities originated from a host cell in the presence of a divalent cation and a stabilizer to thus allow the impurities to undergo agglutination and then removing aggregates thus generated from the human serum albumin-containing solution.

33. The method as set forth in claim 32 wherein the heat-treatment is carried out at a pH value ranging from 9 to 10.

34. A method for producing human serum albumin starting from a raw material obtained through gene engineering operations characterized in that it consists of the steps of heat-treating at a pH value ranging from 5.5 to 10.0 a human serum albumin-containing solution including impurities originated from a host cell in the presence of a divalent cation and a stabilizer to thus allow the impurities to undergo agglutination and then removing aggregates thus generated from the human serum albumin solution.

35. The method as set forth in claim 34 wherein the heat-treatment is carried out at a pH value ranging from 9 to 10.

* * * * *